US006232270B1

(12) United States Patent
Branly et al.

(10) Patent No.: US 6,232,270 B1
(45) Date of Patent: May 15, 2001

(54) AGRICULTURAL COMPOSITIONS CONTAINING BACTERIA

(75) Inventors: Keith Branly, Germantown, TN (US); Rhett Atkins, Georgetown, SC (US)

(73) Assignee: Micro Flo Company, Memphis, TN (US)

( * ) Notice: Subject to any disclaimer, the term of this patent is extended or adjusted under 35 U.S.C. 154(b) by 0 days.

(21) Appl. No.: 09/308,926

(22) PCT Filed: Nov. 29, 1996

(86) PCT No.: PCT/US96/19116

§ 371 Date: Sep. 9, 1999

§ 102(e) Date: Sep. 9, 1999

(87) PCT Pub. No.: WO98/23157

PCT Pub. Date: Jun. 4, 1998

Related U.S. Application Data

(63) Continuation-in-part of application No. 08/453,683, filed on May 30, 1995, now Pat. No. 5,650,372.

(51) Int. Cl.[7] ............................ A01N 43/66; A01N 57/02; A01N 63/00
(52) U.S. Cl. ............................ 504/117; 504/127; 504/130
(58) Field of Search .................................. 504/117, 127, 504/130

(56) References Cited

U.S. PATENT DOCUMENTS

| | | | |
|---|---|---|---|
| 2,921,410 | 1/1960 | Merritt et al. | 47/58 |
| 3,911,110 | 10/1975 | Smirnoff | 424/93 |
| 3,920,812 | 11/1975 | Mann | 424/115 |
| 4,061,488 | 12/1977 | Mann | 71/77 |
| 4,161,397 | 7/1979 | Bellet et al. | 71/7 |
| 4,551,164 | 11/1985 | Tenzer | 71/6 |
| 4,609,550 | 9/1986 | Fitz-James | 424/93 |
| 4,666,497 | 5/1987 | Tenzer | 71/6 |
| 4,695,462 | 9/1987 | Barnes et al. | 424/195.1 |
| 4,762,567 | 8/1988 | Retallick | 106/287.17 |
| 4,764,371 | 8/1988 | Pusey et al. | 424/93 |
| 4,877,738 | 10/1989 | Handelsman et al. | 435/252.5 |
| 4,878,936 | 11/1989 | Handelsman et al. | 71/7 |
| 4,952,229 | 8/1990 | Muir | 71/7 |
| 5,047,239 | 9/1991 | Pusey | 424/93 |
| 5,049,379 | 9/1991 | Handelsman et al. | 424/115 |
| 5,061,490 | 10/1991 | Paau et al. | 424/93 |
| 5,215,747 | 6/1993 | Hairston et al. | 424/93 M |
| 5,221,314 | 6/1993 | Watson et al. | 504/117 |
| 5,288,488 | 2/1994 | Backman et al. | 424/93 D |
| 5,288,624 | 2/1994 | Nielsen | 435/128 |
| 5,364,788 | 11/1994 | Kubo | 435/252.5 |
| 5,403,583 | 4/1995 | Liu et al. | 424/93.46 |
| 5,413,783 | 5/1995 | McLaughlin et al. | 424/93.51 |
| 5,543,301 | 8/1996 | Handelsman et al. | 435/34 |

FOREIGN PATENT DOCUMENTS

| | | |
|---|---|---|
| 2200924 | 8/1988 | (EP) . |
| WO9823157 | 6/1998 | (EP) . |

OTHER PUBLICATIONS

R.S. Utkhede and E.M. Smith, Agriculture Canada, Research Station, Summerland, B.C., Canada VOH iZO; Promotion of apple tree growth fraud production by the EDW–4 strain of *Bacillus subittis* in appled replant group, Jul. 24, 1992.

Jo Handelsman et al., Applied and Environmental Microbiology, Biological Control of Damping–Off of Alfalfa Seedlings with *Bacillus cereus* UW85, vol. 56, No. 3, Mar. 1990.

C.O. Gwathmey, O.M. Wassel, and P.E. Hoskinson; Assistant Professor, Visiting Scientist, and Professor Emeritus, Pix Effects on Earliness and Fruit Retention of Contrasting Cotton Varieties, Department of Plant and Soil Science, University of Tennessee, Jackson, TN, (Abstract) 1994.

D.M. Oosterhuis, L.D. Janes, and B. R. Bondada Professor, Research Assistant and Research Associate, Research Plant Growth Regulators in Cotton Summary of 1994 Results University of Arkansas, Fayetteville,AaR, (Abstract) 1995.

Derrick M. Oosterhuis, Effects of PGR–IV on the Growth and Yield of Cotton: A Review, Department of Agronomy, University of Arkansas, Fayetteville, AR 72701 (Abstract) Feb. 1994.

United States Environmental Protection Agency (EPA), Pesticide Fact Sheet, *Bacillus Subtilis* GB03. 1992.

Robert S. Breed, et al., *Bergey's Manual of Determinative Bacteriology*, The Williams & Wilkins Company, 1957.

*Primary Examiner*—S. Mark Clardy
(74) *Attorney, Agent, or Firm*—Roylance Abrams Berdo & Goodman, L.L.P.

(57) ABSTRACT

An agriculturally effective active ingredient is applied to plant foliage before, after, or simultaneously with an enhancer component containing a substantially pure bacterial culture, suspension, spores, or cells of a bacteria selected from the genus Bacillus or a soil bacteria.

51 Claims, No Drawings

AGRICULTURAL COMPOSITIONS CONTAINING BACTERIA

This application is a national phase application claiming priority to PCT/US96/19116, filed on Nov. 29, 1996, and is a continuation in part of U.S. patent application Ser. No. 08/453,683 filed on May 30, 1995, now U.S. Pat. No. 5,650,372.

FIELD OF THE INVENTION

The invention relates to the treatment of plants by a composition containing an agriculturally effective active ingredient and an enhancer additive containing a substantially pure culture of bacteria selected from the genus Bacillus or a soil bacteria. The added culture may be in the form of cell, spores, or suspensions.

BACKGROUND OF THE INVENTION

Agricultural chemical manufacturers are always looking for ways to improve the efficacy of active ingredients used on plants. This is particularly true where the applied material is a plant growth regulator (growth stunting or growth enhancing) herbicide, or systemic agent (e.g., insecticide or fungicide). Transport mechanisms into the plant and translocation among the various plant tissues is important and, in some instances, may be the primary factor determining the efficacy of the applied ingredient. For some active ingredients, an improvement in the transports mechanism could translate into improved performance at existing application rates, the need for less active ingredient, or the ability to treat new species that were previously resistant to the active ingredient.

Mepiquat chloride is an active ingredient where plant uptake and transport is important. Mepiquat chloride (N,N-dimethylpiperidinium chloride) is used annually as the active ingredient for stunting vegetative cotton plant growth and increasing fruit retention on millions of acres of cotton. Mepiquat chloride also has some uses on potatoes, sweet potatoes, peanuts, grapes, corn, wheat, citrus, tomatoes, and onions.

Mepiquat chloride has the effect on cotton plants of stunting vegetative growth thereby forcing the plant to redirect its energies into fruit (cotton boll) production. With appropriate application of mepiquat chloride to plants that are beginning to exhibit excessive vegetative growth, cotton plant yields can be maintained or increased without harm to the plant. The growth stunting effects are particularly desired when the cop is grown in fertile soil or after weather conditions that favor plant growth rather than fruit production.

Cotton plants have a predictable life cycle and growth period. Cotton plants emerge 7–10 days after the seeds are planted in a furrow. The cotton plant exhibits growth of a root system and the extension of plant height through stem and branch growth in a pattern referred to as "vegetative growth" until about the 4th–8th node. Thereafter, the plant produces a reproductive branch (the "1st fruiting site"), and all subsequent branches are reproductive. Cotton growers attempt to control the growth of the plant to ensure that the ratio of vegetative growth to reproductive growth (boll production) favors the desired range of reproductive growth.

Cotton growers generally prefer to see about 2 inches (5 cm) between main stem nodes. This ratio represents a balance between too much reproductive growth (boll production) which can cause the plant growth to outpace the rate of vegetative growth and terminate before the yield is maximized, and too much vegetative growth which reduces the number of mature bolls.

Cotton plants that have directed the majority of the available plant energy to vegetative growth are referred to as "rank" cotton and produce less bolls which mature later and are vulnerable to weather extremes for longer periods of time. Cotton that exhibits signs of going rank are readily visible by abnormal plant height relative to the boll loads and number of reproductive main stem nodes. Mepiquat chloride is used to stop cotton from going rank by modifying the cotton plant's growth characteristics.

The branches off the main stem generally always extend from alternating sides of the stem. Each branch site is called a "node" with 5–7 nodes being formed above the cotyledon leaves before the first fruit bearing branch with true leaves is formed. Node counting starts at the bottom of the plant and extends up the main stem. The "internode length" is the distance between branch sites with a new node being formed roughly every three days. For purposes of measurement and comparison, the number of nodes and internode length above node 8 are generally used to eliminate interplant fruiting node variations because fruit bearing branches will necessarily have been formed by node 8. The counting of fruiting nodes thus conventionally starts from the first reproductive node, usually no. 7 or no. 8.

Fruiting sites in cotton are referred to as "squares." Each fruit bearing branch will form 1–6, normally about 3, fruiting sites ("squares") with approximately six days between square formations on each branch. New squares and the beginning of reproductive growth in cotton plants are referred to as "pinhead" squares due to their barely visible size. After about 5–10 days, the square has grown to about the size of a match head and is a period in the plant cycle referred to as a "match head square." The match head square continues to grow to about the size of an average adult fingernail before blooming ("early bloom"). Three days later, a boll has formed beneath the bloom. Roughly thirty days after early bloom, the product boll is fully mature and ready for harvest. Overall, about 80% of the total cotton yield is set within the first 3 weeks after early bloom and 95% of the total yield is set within 5 weeks of early bloom.

Generally, mepiquat chloride is applied to cotton plants in one of two ways. The method used until about 1986 was a single application of 8–16 ounces per acre of a 4.2 wt % solution at early bloom. This type of single treatments did control plant height although it was noticed that plant yields were occasionally reduced particularly if the plant was stressed during or after the application.

Since 1987, the trend has been to apply mepiquat chloride in a series of applications each having a lower dose than the single dose application. The first treatment occurs at match head square with a second treatment 7–14 days thereafter. Both treatments are made at a rate within the range from about 0–8 ounces of 4.2 wt % solution per acre with the specific application rate depending on whether the cotton plant was exhibiting signs of being stressed (no application), moderate growth (about 2 ounces of solution per acre), or vigorous growth (about 4 ounces of solution per acre). Thereafter, two additional treatments at 7–14 day intervals may be used with application rates extending up to about 8 ounces of 4.2 wt % mepiquat chloride solution with the specific application rate dependent on the amount of vegetative growth in the field. Further experimentation by individual growers has resulted in a wide variety of multiple application rates.

It would be desirable if the use of mepiquat chloride could be integrated into a system of treatment that would increase plant tissue mass in the roots, stems, and leaves to provide higher levels of nutrient transfer while, at the same time, restricting vegetative growth to enhance fruit production.

The technology of plant herbicides has a continuing desire for enhanced efficacy without a corresponding increase in the application rate. Many herbicides could also use a boost in activity without an increase in the amount of applied herbicide. Farmers and herbicide manufacturers are often faced with a need to control weeds and noxious plants without exceeding the application levels of proven herbicides, if the plants can be controlled at all. Some plants, like Florida Pusley, Bull Grass, Bermuda grass, Dog Fennel, and Primrose are all highly resistant to herbicides proven to be effective.

It would be useful to have a means for increasing the efficacy of agriculturally active ingredients, such as herbicides, without increasing the amount of the applied active ingredient.

SUMMARY OF THE INVENTION

It is an objective of the present invention to provide a composition and method of use therefore to increase the efficacy of agriculturally effective active ingredients.

It is a further objective of the invention to provide a composition and method for its use on fruit-producing plants and seeds that increases the number of fruiting sites on treated plants with the goal of providing increased yields of fruit.

It is another objective of the invention to provide a composition and method for its use in which treated plants grow in a more healthy condition.

In accordance with these and other objectives of the invention that will become apparent from the description herein, a composition according to the invention comprises: (a) an agriculturally effective active ingredient, and (b) an enhancer containing a culture containing bacteria from the genus Bacillus or a soil bacteria in the form of cells, cultures, or suspensions and in an amount sufficient to enhance the effectiveness of said active ingredient. Preferably, the enhancer is free of plant growth hormones when used in combination with plant growth stunting agents, like mepiquat chloride, that suppress plant growth hormones in the treated plant.

Compositions according to the present invention improve the efficacy of the applied agriculturally active ingredient. The same amount of active material that is conventionally applied will be more effective. Lower levels of active ingredient can be used to achieve the same effect as the higher conventional application rate. In addition, plants that have treated with compositions according to the invention are healthier with the attendant benefit of being more resistant to disease or other stress as well as exhibiting higher numbers of fruiting sites and increased yields.

DETAILED DESCRIPTION

The invention provides a method for treating plants with a composition containing an agriculturally effective active ingredient and an enhancer containing a culture of a bacteria selected from the genus Bacillus or a soil bacteria in an amount sufficient to enhance the effectiveness of an agriculturally effective active ingredient applied simultaneously, before, or after application of the enhancer. The increased effectiveness attributable to the bacteria-containing enhancer component can be used to reduce the amount of applied agriculturally effective active ingredient or, when the active ingredient is applied at the same rate, the bacillus increases the effectiveness of the applied agriculturally effective active ingredient. Such increased effectiveness is useful for controlling weeds that are otherwise difficult to control with regular herbicides.

The Bacteria-Containing Enhancer

The enhancer component contains spores, cultures, and suspensions of a bacteria from the genus Bacillus or a soil bacteria. Preferably, the bacteria for the enhancer component is in the form of spores as a result of a suitable adjustment in temperature, pH, salinity, etc.

Suitable bacteria for use in the present invention include those bacteria that exhibit an ability to increase the effectiveness of an agriculturally effective active ingredient by any mechanism. Methods for screening bacterial strains for bioactivity and therefore their capacity to enhance the effectiveness of a plant growth regulator, a herbicide, a systemic fungicide, or a systemic insecticide will be apparent to one of ordinary skill in the art in view of the disclosure and examples set forth herein. For example, a candidate bacterial strain, such as a *Bacillus cereus*, can be cultured and maintained under standard laboratory conditions. (See e.g., Sambrook et al. "Molecular Cloning: A Laboratory Manual" Cold Spring Harbor Laboratory press (1989)). Specific plants can be chosen for their susceptibility or resistance to a particular agriculturally effective compound such as a herbicide or a plant growth regulator. For example, and as set forth in the Example section contained herein, cotton can be used to evaluate the bioactivity of a bacterial strain in combination with a plant growth regulator as reflected in the number of fruiting sites and/or the number of bolls produced and compared to treating similar plants with only the plant growth regulator or the bacteria. Alternatively, plants susceptible to certain fungal diseases, such as tomato leaf blight, potato scab, wheat stem rust, corn smut, or leaf rust of various plant species, can be grown under controlled conditions and treated either with an appropriate fungicide, a fungicide with a candidate bacteria species, or the bacterial species alone, either before, concurrently, or subsequent to controlled inoculation of the plants with the disease causal organism, to evaluate the capacity of the bacterial species to enhance the activity of the fungicide. These types of experiments can be carried out in the field, under semi-controlled conditions such as a greenhouse, or under relatively controlled conditions such as within a growth chamber. These experiments involve routine screening of organisms for their enhancement effect with compounds or compositions on known plant species, and the parameters used to evaluate the effects are likewise known and routinely measured.

These similar types of screens can be utilized with bacterial strains described herein to provide an enhancement effect to a particular agriculturally effective active ingredient, i.e., the *Bacillus cereus* strain deposited with the American Type Culture Collection as ATCC 55675 providing an enhancement effect to the plant growth regulator mepiquat chloride and the herbicide atrizine, to screen the bacterial species for potential enhancement with other agriculturally effective active ingredients, such as systemic insecticides and systemic fungicides.

Particularly preferred are cultures, spores, and suspensions of soil bacteria encountered between and among the roots of thriving growths of the plant type in the local soil. Foliar application of the local soil bacteria at an application rate within the range from about $0.1\times10^{10}$ CFU/acre to about $10\times10^{10}$ CFU/acre enhances the natural mechanisms associated with plant growth and propagation to a level sufficient that the agriculturally active ingredient exhibits enhanced activity on or within the treated plant.

A wide variety of bacterial species within the genus Bacillus and within the known species of soil bacteria are useful within the present invention. The following is a list of species for the present invention:

Bacteria from the genus Bacillus

*Bacillus acidocaldarius*
*Bacillus acidoterrestris*
*Bacillus alcalophilus*
*Bacillus alvei*
*Bacillus aminoglucosidicus*
*Bacillus aminovorans*
*Bacillus amyloliquefaciens*
*Bacillus amylolyticus*
*Bacillus anthracis*
*Bacillus aneurinolyticus*
*Bacillus apiarius*
*Bacillus azotofixans*
*Bacillus brevis*
*Bacillus badius*
*Bacillus capitovalis*
*Bacillus cereus*
*Bacillus circulans*
*Bacillus cirroflagellosus*
*Bacillus coagulans*
*Bacillus colofoetidus*
*Bacillus cycloheptanicus*
*Bacillus epiphytus*
*Bacillus fastidiosus*
*Bacillus filicolonicus*
*Bacillus firmus*
*Bacillus freudenreidii*
*Bacillus fructosus*
*Bacillus globigii*
*Bacillus globisporus*
*Bacillus insolitus*
*Bacillus laevolacticus*
*Bacillus larvae*
*Bacillus laterosporus*
*Bacillus lautus*
*Bacillus lentimorbus*
*Bacillus lentus*
*Bacillus licheniformis*
*Bacillus macerans*
*Bacillus macquariensis*
*Bacillus maroccanus*
*Bacillus macroides*
*Bacillus medusa*
*Bacillus megaterium*
*Bacillus mycoides*
*Bacillus natto*
*Bacillus nigrificans*
*Bacillus pabuli*
*Bacillus pacificus*
*Bacillus pantothenticus*
*Bacillus parabrevis*
*Bacillus pasteurii*
*Bacillus polymyxa*
*Bacillus popilliae*
*Bacillus pulvifa*
*Bacillus pulvifaciens*
*Bacillus pumilus*
*Bacillus prodigiosus*
*Bacillus psychrophilus*
*Bacillus psychrosaccharolyticus*
*Bacillus racemilacticus*
*Bacillus sphaericus*
*Bacillus stearothermophilus*
*Bacillus subtilis*
*Bacillus thermodenitrificans*
*Bacillus thiaminolyticus*
*Bacillus thuringiensis*
*Bacillus uniflagellatus*
*Bacillus validus*

Soil Bacteria

*Achromobacter pestifer*
*Alcaligenes eutrophus*
*Alcaligenes latus*
*Amycolata autotrophica*
*Archangium gephyra*
*Arthrobacter viscosus*
*Azotobacter chroococcum*
*Bacillus acidovorans*
*Bacillus brevis*
*Bacillus cereus*
*Bacillus circulans*
*Bacillus insolitus*
*Bacillus laterosporus*
*Bacillus megaterium*
*Bacillus mojavensis*
*Bacillus mycoides*
*Bacillus pasteurii*
*Bacillus polymyxa*
*Bacillus psychrosaccharolyticus*
*Bacillus sphaericus*
*Bacillus subtilis*
*Bacillus viscosus*
*Chainia hygroatrocyanea*
*Clostridium absonum*
*Cystobacter fuscus*
*Cytophaga johnsonae*
*Ensifer adhaerens*
*Hyphomicrobium facilis*
*Microccus luteus*
*Micromonospora chalcea*
*Micromonospora coerulea*
*Micromonospora grisea*
*Micromonospora polytrota*
*Microtetraspora glauca*
*Mycobacterium agri*
*Mycobacterium aichiense*
*Mycobacterium aurum*
*Mycobacterium chitae*
*Mycobacterium chubuense*
*Mycobacterium diernhoferi*
*Mycobacterium fortuitum*
*Mycobacterium neoaurum*
*Mycobacterium parafortuitum*
*Mycobacterium terrae*
*Mycobacterium thermoresistibile*
*Myxococcus coralloides*
*Myxococcus fulvus*
*Myxococcus macrosporus*
*Myxococcus xanthus*
*Nannocystis exedens*
*Nitrosolobus multiformis*
*Nocardia brasiliensis*
*Nocardioides albus*
*Ochrobactrum anthropi*
*Polyangium cellulosum*

| | |
|---|---|
| Pseudomonas aeruginosa | ATCC 15575 |
| Pseudomonas fluorescens | ATCC 27505 |
| Pseudomonas glathei | ATCC 21697 (*Achromobacter nitriloclastes*) |
| Rahnella aquatilis | ATCC 15811 |
| Saccharobacterium acuminatum | ATCC 4925 (*Bacillus nigrificans*) |
| Saccharomonospora viridis | ATCC 27370 |
| Serratia marcescens | ATCC 6051a |
| Streptomyces anandii | ATCC 7003 |
| Streptomyces aureofaciens | ATCC 11838 |
| Streptomyces chartreusis | ATCC 15563 |
| Streptomyces cyaneus | ATCC 33234 |
| Streptomyces cymarogenes | ATCC 25369 |
| Streptomyces diastatochromogenes | ATCC 27689 |
| Streptomyces flavogriseus | ATCC 55033 |
| Streptomyces gelaticus | ATCC 13933 |
| Streptomyces hygroscopicus | ATCC 15244 |
| Streptomyces indigocolor | ATCC 27328 |
| Streptomyces katrae | ATCC 12695 |
| Streptomyces lipmanii | ATCC 12100 |
| Streptomyces longisporus | ATCC 21554 |
| Streptomyces massasporeus | ATCC 21555 |
| Streptomyces nobilis | ATCC 15561 |
| Streptomyces odorifer | ATCC 15562 |
| Streptomyces omiyaensis | ATCC 9799 |
| Streptomyces parvulus | ATCC 12711 |
| Streptomyces phaeochromogenes | ATCC 14593 |
| Streptomyces pseudogriseolus | ATCC 4944 |
| Streptomyces roseoflavus | ATCC 31002 |
| Streptomyces rubiginosohelvolus | ATCC 31004 |
| Streptomyces rutgersensis | ATCC 9943 |
| Streptomyces sclerogranulatus | ATCC 13407 |
| Streptomyces toxytricini | ATCC 7067 |
| Streptomyces violaceoruber | ATCC 29056 |
| Streptomyces violaceus | ATCC 31524 |
| Streptomyces violarius | ATCC 31526 |
| Thermoactinomyces vulgaris | ATCC 21359 |
| Thiobacillus denitrificans | ATCC 21360 |
| Thiobacillus thioparus | ATCC 13954 |
| non-fluorescent Pseudomonas | ATCC 13955 |
| Rhizobium | ATCC 15044 |
| Agrobacterium | ATCC 33677 |
| Corynebacterium ureafaciens | ATCC 31003 |
| Arthrobacter ureafaciens | ATCC 31522 |
| Pseudomonas aeruginosa | ATCC 465 N. |
| Bacillus fastidosus | ATCC 12432 |
| Micrococcus dentrificans | ATCC 43223 |
| Mycobacterium phlei | ATCC 13952 |
| Aerobacter aerogenes | ATCC 13953 |
| Fusarium moniliforme | ATCC 14662 |
| Histoplasma capsulata | ATCC 15039 |
| Penicillinum chyrsogenum | ATCC 15040 |

Particularly useful are species of *B. subtilis*, *B. cereus*, and *B. megaterium*. *Bacillus subtilis* and *B. cereus* are naturally occurring soil saprophytes found throughout the world. In the 1992 edition of the American Type Culture Collection, 182 different strains of *B. subtilis* are listed and incorporated herein by reference. The following is a list of *B. subtilis* that would be useful in the present invention:

*B. subtilis*

ATCC 10783
ATCC 15818
ATCC 15819
ATCC 15245 (*Bacillus natto*)
ATCC 15134 (*Bacillus uniflagellatus*)
ATCC 13542
ATCC 13472
ATCC 15041
ATCC 15042
ATCC 15043
ATCC 15181
ATCC 15182
ATCC 15183
ATCC 15184
ATCC 21183
ATCC 21336
ATCC 49343
ATCC 6537
ATCC 21394
ATCC 8473
ATCC 31523
ATCC 31525
ATCC 31527

ATCC 29233
ATCC 14660
ATCC 14661
ATCC 31268
ATCC 4925
ATCC 55405
ATCC 9524
ATCC 15476
ATCC 23858
ATCC 23859
ATCC 7060
ATCC 7058
ATCC 7059
ATCC 7480 (*Bacillus endoparasiticus*).
ATCC 21584
ATCC 31022
ATCC 21331
ATCC 21332
ATCC 21777
ATCC 21778
ATCC 6598 (*Bacillus licheniformis*)
ATCC 49822
ATCC 23857
ATCC 19221
ATCC 9858
ATCC 21742
ATCC 4529
ATCC 35148
ATCC 33608
ATCC 19549
ATCC 19550
ATCC 21556
ATCC 31340
ATCC 49760
ATCC 53325
ATCC 14807
ATCC 21228
ATCC 15512
ATCC 15841
ATCC 10774
ATCC 31091
ATCC 31092
ATCC 31094
ATCC 31096
ATCC 31097
ATCC 39546
ATCC 39374
ATCC 11774
ATCC 15116
ATCC 35021
ATCC 31954
ATCC 19062
ATCC 23059
ATCC 53115
ATCC 15115
ATCC 13956
ATCC 21952
ATCC 82
ATCC 21603
ATCC 31785
ATCC 21697
ATCC 15477
ATCC 31098
ATCC 19162
ATCC 14617
ATCC 14618
ATCC 33713
ATCC 33714
ATCC 55422
ATCC 6461
ATCC 21007
ATCC 21770
ATCC 6984
ATCC 19163
ATCC 21663
ATCC 19217
ATCC 19219
ATCC 19220
ATCC 21005
ATCC 21006

A preferred *B. subtilis* strain for use in the present invention includes GB03. Previously, *B. subtilis* GBO3 was recognized as a biological fungicide and commercially used as a seed treatment under the names KODIAK™ HB or GUS 2000™ by Gustafson, Inc., Plano, Tex. 75093 (EPA Reg. No. 7501-146). This product is available as a 2.75% powder formulation containing not less than $5.5 \times 10^{10}$ viable spores per gram and is to be applied at a rate ranging from 2–4 ounces per 100 pounds of seed. The use directions indicate that the product is to be used for treatment of crop seeds only. This strain is said to colonize the developing root systems and compete with disease organisms that would attack the roots. Foliar application is not listed.

The following is a list of *B. cereus* that would be useful in the present invention.

*B. cereus*

ATCC 55675 (BP01)
ATCC 13824 NCIB 2600 (*Bacillus cereus* var. fluorescens)
ATCC 14603
ATCC 15816
ATCC 15817
ATCC 13472
ATCC 14737
ATCC 9592 (*Bacillus metiens*).
ATCC 27877
ATCC 19637
ATCC 11950
ATCC 23261
ATCC 6464
ATCC 11773 (*Erwinia atroseptica*).
ATCC 10876
ATCC 10987
ATCC 4342 (*Bacillus lacticola*).
ATCC 21182
ATCC 7004 (*Bacillus albolactis*).
ATCC 10702
ATCC 12480
ATCC 49063
ATCC 2 (*Bacillus agri*)
ATCC 19265 (*Bacillus cereus* subsp. alesti)
ATCC 21634
ATCC 12826
ATCC 21768
ATCC 21769
ATCC 21771
ATCC 21772
ATCC 9139
ATCC 21928
ATCC 27522
ATCC 31430
ATCC 43881
ATCC 246 (*Bacillus lactimorbus*).
ATCC 21770 (*Bacillus cereus*).

ATCC 21929 (*Bacillus cereus*).
ATCC 13367
ATCC 31429
ATCC 31293
ATCC 21366 (*Bacillus coagulans*)
ATCC 25621 (*Bacillus medusa*)
ATCC 7039 (*Bacillus metiens*)
ATCC 14893 (*Bacillus subtilis*).
ATCC 9818 (*Bacillus lactis*)
ATCC 33018
ATCC 33019
ATCC 55055
ATCC 53522
ATCC 13366
ATCC 7064 (*Bacillus siamensis*)
ATCC 11949
ATCC 10792 (*Bacillus cereus*)
ATCC 27348
ATCC 23260 (*Bacillus endorhythmos*)
ATCC 13061
ATCC 13062 (*Bacillus megaterium*)
ATCC 25972
ATCC 14579
ATCC 19646
ATCC 49064
ATCC 11778
ATCC 39152

ATCC 19146 FDA Strain PCI 818 (Pseudomonas sp.)

A preferred *B. cereus* strain for use in the present invention includes strain ATCC No. 55675. In another embodiment, the *B. cereus* strain for use in the present invention has the characteristics as ATCC No. 55675. In yet another embodiment, the *B. substilis* strain for use in the present invention has the characteristics as ATCC No. 55675.

The following is a list of *B. megaterium* that would be useful in the present inventions:

*B. Megaterium*

ATCC 33166
ATCC 33167
ATCC 33168
ATCC 33169
ATCC 12872
ATCC 33164
ATCC 11478
ATCC 33165
ATCC 11561
ATCC 11561a
ATCC 11561b
ATCC 11561c
ATCC 11561d
ATCC 11561e
ATCC 6458
ATCC 6459
ATCC 14946
ATCC 27327
ATCC 33729
ATCC 9885
ATCC 13639
ATCC 13632
ATCC 15374
ATCC 49099
ATCC 49096
ATCC 43725
ATCC 19136
ATCC 25848
ATCC 4531
ATCC 13402
ATCC 15046
ATCC 15047
ATCC 25300
ATCC 19390
ATCC 13368
ATCC 21181
ATCC 35985
ATCC 39383
ATCC 11562
ATCC 15127
ATCC 15128
ATCC 7703
ATCC 14945
ATCC 15177
ATCC 19218
ATCC 25833
ATCC 15450
ATCC 19135
ATCC 19137
ATCC 21916
ATCC 8245
ATCC 15781
ATCC 31294
ATCC 15117
ATCC 15118
ATCC 19160
ATCC 19161
ATCC 89
ATCC 21209
ATCC 35076
ATCC 49098
ATCC 39118
ATCC 7051
ATCC 7052
ATCC 10778
ATCC 8011
ATCC 7056
ATCC 14581
ATCC 13062
ATCC 49097
ATCC 19213
ATCC 71
ATCC 35075
ATCC 21603
ATCC 21738
ATCC 72
ATCC 21737
ATCC 49095
ATCC 15451

The Active Ingredients

Agriculturally effective ingredients used in the present invention can be selected from a wide variety of materials that act on and through the metabolism of the treated plants. For premixed materials, it is desirable to select active ingredients that do not degrade or otherwise become impaired by extended storage at the conditions used to maintain the bacteria-containing enhancer component in a spore form.

The general term "plant growth regulating agent" encompasses a number of active ingredients that affect a plant in different ways. Generally speaking, plant growth regulators encompass plant growth stunting agents, plant growth enhancing agents, and herbicides.

Suitable plant growth enhancing agents for the present invention include plant growth hormones such as at least one of the 84 identified gibberillins with $GA_3$, $GA_4$, $GA_5$, $GA_7$ and $GA_9$ being preferred; cytokinins (e.g., zeatin, kinetin, benzyladenine, dihydrozeatin, and isopentenyl adenine); auxins (e.g., indolacetic acid (IAA), indolebutyric acid (IBA), and naphthalenacetic acid (NAA)); sodium ortho-nitrophenolate; sodium para-nitrophenolate; sodium 5-nitro-guaicolate; polyhydroxycarboxylic acids of 2, 4, 5, and 6 carbon structures; ethephon; and a variety of nitrogen or phosphorous-containing fertilizers.

Suitable plant growth stunting agents useful in the invention include chlormequat chloride, mepiquat chloride, as well as maleic hydrazide and its esters. Such plant growth regulators affect and alter plant metabolic processes to enhance or retard plant growth. All such agents can be used according to the application rates and timing specified by the manufacturer on the product label.

Herbicides include the triazines (e.g., atrazine), the ureas, glyphosate, sulfosate, glyfosinate, and sethoxydim.

Suitable systemic agents that will benefit from enhanced plant uptake, transport, and process assimilation include the systemic pesticides and systemic fungicides. Systemic agents for plants that benefit from the present invention include, inter alia, the insecticides aldicarb, acephate, carbofuran, dimethoate, phorate, and terbufos.

Systemic fungicides that will benefit from the mixtures of the invention include tridemorph, metalaxyl, iprodione, fosetyl-aluminum, thiophanate, benomyl, triadimefon, carboxin, oxycarboxin, carbendazim, thiabendazole, thiophanate, ethirimol, bupirimate, and dimethirimol.

Plants that can be treated by the present invention include virtually any plant grown in soil and that is affected by an agriculturally effective active ingredient. Exemplary plants include commodity grain crops (e.g., corn, wheat, and soybeans), sorghum, desired and undesired grasses, weeds, herbs, etc.

The invention is well suited to increased production of fruit in plants that produce fruiting sites from which fruit will grow. Such plants preferably include any of the raw agricultural commodity and especially cotton, soybeans, peanuts, grapes, apples, citrus (e.g., lemons, limes, oranges, grapefruit), berries (e.g., strawberries, blackberries, raspberries), tubers (e.g., potatoes, sweet potatoes), corn, cereal grains (e.g., wheat, rice, rye), tomatoes, onions, cucurbits (e.g., watermelon, cucumbers, and cantaloupes).

Method of Use

The compositions of the present invention may take the physical form of a liquid, emulsion, suspension, solid granule, aggregate, or composite granule (e.g., active ingredient solids carried on an inert carrier particle). Application of each physical form to plant foliage will generally proceed with conventional techniques.

Gram positive bacteria strains can be used in the enhancer component in the form of cells, spores, cultures, or suspensions thereof. In a liquid or dispersible solid forms, the enhancer is added to a spray tank or other form of liquid distribution reservoir as a stable, aqueous concentrate solution exhibiting an equivalent spore concentration within the range from about 300,000 colony forming units per milliliter (CFU/ml) to about 1.5 million CFU/ml, preferably about 1 million to about 1.2 million CFU/ml to make a composition that is applied to plant foliage at a rate within the range from about $0.1 \times 10^{10}$ CFU/acre to about $100 \times 10^{10}$ CFU/acre, preferably at a rate within the range from about $0.1 \times 10^{10}$ CFU/acre to about $10 \times 10^{10}$ CFU/acre, and most preferably within the range from about $0.5 \times 10^{10}$ CFU/acre (0.5 fl. oz./acre of concentrate) to about $8 \times 10^{10}$ CFU/acre (2 fl. oz./acre of concentrate). Optionally and in a preferred embodiment, the spray tank will also contain the agriculturally effective active ingredient component for simultaneous application of both components.

Solid forms of the components can be dry mixed or formed into aggregates before broadcast. One or more of the conventional adjuvants may be used to enhance dispersion, breakdown, adhesion to foliage, etc.

The specific application rate can vary somewhat depending on the method by which the solution is to be applied to the plant surfaces. For example, aerial spraying will employ a different dilution rate and application quantity than boom spraying, manual sprayers, or broadcast of granules. Conventional equipment can be used for the application. If desired, the enhancer component can be mixed with other treatments and applied simultaneously or can be applied in a discrete treatment step. Foliar application is the preferred method for increasing the number of fruiting sites on fruit-producing plants.

The concentrate can also be used to formulate a ready-to-use, packaged mixture. So prepared, the enhancer is diluted to an amount in the package container that is within the range from about 150,000 CFU/ml to about 600,000 CFU/ml and with conditions adequate to ensure that the bacterial component remains in a spore form but will become vegetative after application.

For many bacteria, use of a pH of less than 7 (i.e., acidic) will maintain the bacteria in a spore form. If necessary, any of the conventional acidifying agents or buffers (preferably food grade or those classified as "Generally Regarded As Safe" by the U.S. Environmental Protection Agency) may be used to maintain a suitable acidic pH to ensure storage stability. Under such acidic conditions, the spores remain stable and exhibit good storage stability. When diluted for use and following application, the pH of the solution will raise to greater than 7 thereby causing the bacteria in the enhancer to become live, vegetative colonies. The bacteria will thereby reproduce on the treated plant surfaces and facilitate or translocation of the agriculturally effective active ingredient.

The bacteria-containing enhancer component can be applied as a discrete treatment or simultaneously with a variety of other agriculturally effective active ingredients. Useful agriculturally effective active ingredients include plant growth enhancing agents, plant growth stunting agents, herbicides, systemic insecticides, and systemic fungicides. Preferably, the composition is a combination of either a plant growth stunting agent or herbicide and an enhancer containing a substantially pure strain of B. subtilis, B. cereus, or ATCC 55675 (BP01) applied at the rate of at least $0.1 \times 10^{10}$ CFU/acre.

In a particularly preferred embodiment, a gibberellin-free enhancer containing the bacillus is applied to the foliage of cotton plants at the same time the plants are treated with mepiquat chloride. An aqueous tank mixture containing the bacteria-containing enhancer (preferably ATCC 55675) and mepiquat chloride is a convenient method for simultaneously applying the components. If premixed, the mepiquat achloride and bacteria-containing enhancer can be stored readily at a pH within the range from about 4–6.5, most preferably within the range of about 5–6.5.

It should be noted that formulations according to the present invention desirably do not include combinations of materials that attempt to act in a contradictory fashion on the plant metabolism. For example, mepiquat chloride is commonly used on cotton foliage to suppress plant growth hormones and stunt the vegetative growth of the plant. A formulation would preferably not be prepared that included plant growth hormones because the effects of the mepiquat chloride and the growth hormones would place inconsistent demands on the plant metabolism, reduce the efficacy of the mepiquat chloride, and lead to inconsistent results. With the present invention, however, the combination of mepiquat chloride and ATCC 55675 consistently produces treated plants that have higher yield, more healthy growth, and a higher resistance to disease.

While not wishing to be bound by any particular theory of operation and with respect to the combined use of the bacteria-containing enhancer and mepiquat chloride on cotton, the bacteria appears to be affecting the plant growth mechanism to increase the retention of bolls on fruiting sites 1 and 2 and increasing the number of bolls overall by producing and retaining fruiting sites on normally vegetative branches.

For the present invention, mepiquat chloride is used at the application rates and during the conventional stages of cotton plant growth. Conventionally applied rates of mepiquat chloride are up to about 60 g/acre (25 g/acre) or about 1–16 ounces per acre with individual application rates falling within the range from about 2.5 g/acre (1.0 g/hectare) for a 2 ounce/acre application of 4.2 wt % solution to 10 g/acre (4.1 g/hectare) for an 8 ounce/acre application of the same 4.2 wt % solution. If mepiquat chloride of higher or lower purity and/or activity is used, the specific application rate should be adjusted up or down according to the change in conventional mepiquat chloride activity.

EXAMPLES

Example 1

An aqueous mixture of 4.2 wt % mepiquat chloride and 560,000 CFU/ml *B. cereus* (lab sample BP01, ATCC 55675) was prepared in a 1:1 volumetric ratio. This solution was applied by conventional sprayer in four applications to the foliage of growing cotton plants in test areas of fields A (10 of 50 acres in Mississippi) and B (8 of 60 acres in Tennessee). Field A was treated with one dose at the range of 4 fluid ounces per acre followed in five weeks by a treatment at the rate of 8 fluid ounces per acre.

Field B received a different treatment regiment. The first three applications in Field B were at the rate of 4 fluid ounces per acre. (The first and second were 24 days apart. The second and third were at 6 days apart). The final application in Field B was at the rate of 8 fluid ounces per acre 11 days later. In all cases, the control fields were treated with the same rate of only mepiquat chloride.

After treatment, sampling in Fields A and B was conducted by hand of representative rows. All known biases were placed in favor of the control treatment with only mepiquat chloride.

In Fields A and B, beginning and final plant heights of the treated cotton plants was measured. The total plant heights of the control fields was comparable to those treated according to the invention. See, Table 1.

TABLE 1

| Field | Beginning Height (in.) | Final height (in.) |
|---|---|---|
| A - Control | 293 | 601 |
| A - Treated | 291 | 597 |
| B - Control | 338 | 580 |
| B - Treated | 334 | 636 |

During the growing season, the differences between the control and treated plants were readily observed. When the young plants contained only squares in the first month of fruiting, an unusually high number and size of additional fruiting branches were seen where the primary fruiting branch exits the main stem. Many were as large or almost as large as the primary fruiting branch and contained fruit prior to first bloom. Extra fruit was also observed at the intersection of the fruiting branches and main stem.

As the bloom extended up the plant and only bolls or missing sites were found below the bloom, an unexpected amount of back fruiting was also observed. Double fruiting was observed in squares, blooms, small bolls, and "now open bolls" (rare). Although double fruiting occurred in both the control and treated plants, the instances were higher in the treated plants.

About 3–4 weeks before the end of the growing period, the plants were inspected for the number of fruiting sites, the number of bolls on nodes 1 and 2, as well as the type of boll. Table 2 reports the results of that inspection.

TABLE 2

| Field | Sites | Bolls | % | Open Bolls | Open + Green | Other Bolls |
|---|---|---|---|---|---|---|
| A - Control | 240 | 115 | 48 | 73 | 270 | 25 |
| A - Treated | 292 | 155 | 53 | 173 | 359 | 103 |
| B - Control | 344 | 207 | 60 | — | — | 81 |
| B - Treated | 366 | 234 | 64 | — | — | 163 |

In Field B and at the end of the test period, 20 plants were inspected. The plants were at cut-out. There were no open bolls in the control group and only 7 in the treated group. The younger fruit, however, were larger and older for the treated plants compared to the control plants. This indicates that the treated plants were growing at a faster and more favorable rate. The treated plants had a total of 265 bolls compared to 238 bolls for the control group, an improvement of 11%.

The treated plants also exhibited an increase in the number of fruit on the vegetable branches in the ratio of 86:50 (72% increase). The treated plants also produced an increase in other fruit, i.e., those on fruiting branch positions 3 and wider, at the ratio of 86:50 (72% increase). The estimated weight (seed cotton) of the fruit from the 20 plants was also higher in the treated plants, 1796 g. v. 1456 g. (23% increase).

The extra fruit on the plants brought an expectation that the additional plant parts and young fruit would be a drain on the plant's system. Bolls would open sooner, but would adversely affect yield. This expectation was not realized. The treated plants grew at a faster rate and in a more healthy condition than the control.

To reduce bias, all link was then harvested by hand from the test fields including unfluffed lint from partially opened bolls. Such unfluffed lint are usually from bolls that never opened correctly and are low on the plant or from bolls just opening that are high on the plant. Table 3 reports the weight of seed cotton and the number of green bolls per 10 foot of row in the treated and control fields.

TABLE 3

| Field | Seed cotton (g.) | Number of Green Bolls |
|---|---|---|
| A - Control | 5322 | 97 |
| A - Treated | 6287 | 0 |
| B - Control | 4532 | 175 |
| B - Treated | 5058 | 42 |

The test results show that the combination of mepiquat chloride applied simultaneously with an enhancer containing ATCC 55675 according to the invention produces higher cotton yields and healthier plants than use of mepiquat chloride alone.

Example 2

*Bacillus cereus* strain BP01 (ATCC 55675) was used in combination with a widely used herbicide, atrazine, to determine whether the BP01 would affect control over weeds that are recognized as difficult to fill with triazines. Atrazine is used to provide season-long control in corn, sorghum, and other crops at a suggested rate of 2 pounds active ingredient per acre. At sufficiently high rates, such as those used in this example, atrazine is recognized for its ability to provide nonselective weed control.

In sandy soil, three replicates of each test were performed in 12 ft.×25 ft. plots using a randomized complete block pattern. The weeds were 2–6 inches (5–15 cm) in height at the time of treatment. Atrazine was applied from aqueous solution at rates equivalent to either 1 or 2 pounds of active ingredient per acre. BP01 concentrate was added to the atrazine in an amount equivalent to either 0.5 or 1 fluid ounce per acre (0.5–$1\times10^{10}$ CFU per acre). For comparison, crop oil concentrate (about 85% paraffinic oil and about 17% surfactant) was used as is conventional with triazine herbicides to increase their efficacy. Tables 4–8 report the degree of control for Florida Pusley (Table 4), Bull Grass (Table 5), Bermuda grass (Table 6), Dog Fennel (Table 7), and Primrose (Table 8).

TABLE 4

Florida Pusley

| Treatment | % Control After Treatment 4 days | 9 days | 16 days | 23 days |
|---|---|---|---|---|
| Control | 0 | 0 | 0 | 0 |
| Atrazine (1 lb.) | 3 | 33 | 42 | 45 |
| Atrazine (2 lb.) | 17 | 57 | 72 | 83 |
| Atrazine (1 lb) + crop oil conc. (1 gal.) | 28 | 62 | 68 | 68 |
| Atrazine (1 lb) + 0.5 oz. BP01 | 27 | 43 | 60 | 60 |
| Atrazine (1 lb) + 1 oz. BP01 | 22 | 53 | 65 | 67 |

TABLE 5

Bull Grass

| Treatment | % Control After Treatment 4 days | 9 days | 16 days | 23 days |
|---|---|---|---|---|
| Control | 0 | 0 | 0 | 0 |
| Atrazine (1 lb.) | 10 | 40 | 40 | 55 |
| Atrazine (2 lb.) | 25 | 70 | 80 | 90 |
| Atrazine (1 lb) + crop oil conc. (1 gal.) | 25 | 40 | 65 | 60 |
| Atrazine (1 lb) + 0.5 oz. BP01 | 35 | 40 | 55 | 63 |
| Atrazine (1 lb) + 1 oz. BP01 | 30 | 60 | 80 | 90 |

TABLE 6

Bermuda grass

| Treatment | % Control After Treatment 4 days | 9 days | 16 days | 23 days |
|---|---|---|---|---|
| Control | 0 | 0 | 0 | 0 |
| Atrazine (1 lb.) | 0 | 10 | 15 | 15 |
| Atrazine (2 lb.) | 8 | 15 | 22 | 27 |
| Atrazine (1 lb) + crop oil conc. (1 gal.) | 25 | 27 | 30 | 43 |
| Atrazine (1 lb) + 0.5 oz. BP01 | 7 | 20 | 37 | 68 |
| Atrazine (1 lb) + 1 oz. BP01 | 10 | 23 | 53 | 63 |

TABLE 7

Dog Fennel

| Treatment | % Control After Treatment 4 days | 9 days | 16 days | 23 days |
|---|---|---|---|---|
| Control | 0 | 0 | 0 | 0 |
| Atrazine (1 lb.) | 15 | 40 | 55 | 60 |
| Atrazine (2 lb.) | 17 | 55 | 70 | 95 |
| Atrazine (1 lb) + crop oil conc. (1 gal.) | 25 | 75 | 93 | 98 |
| Atrazine (1 lb) + 0.5 oz. BP01 | 33 | 88 | 96 | 99 |
| Atrazine (1 lb) + 1 oz. BP01 | 30 | 90 | 97 | 100 |

TABLE 8

Primrose

| Treatment | % Control After Treatment 4 days | 9 days | 16 days | 23 days |
|---|---|---|---|---|
| Control | 0 | 0 | 0 | 0 |
| Atrazine (1 lb.) | 10 | 40 | 50 | 60 |
| Atrazine (2 lb.) | 30 | 65 | 70 | 80 |
| Atrazine (1 lb) + crop oil conc. (1 gal.) | 20 | 83 | 88 | 93 |
| Atrazine (1 lb) + 0.5 oz. BP01 | 20 | 60 | 72 | 88 |
| Atrazine (1 lb) + 1 oz. BP01 | 23 | 70 | 65 | 80 |

From Tables 4–8, it can be seen that BP01 generally improve the effectiveness of the atrazine at 23 days after treatment. The control rate at 1 lb. of atrazine with the bacillus was better than the control rate of 2 lb. atrazine for Bermuda grass, Dog Fennel, and Primrose, and the two treatments has the same control rate for Bull Grass. Only with Florida Pusley and 1 lb/acre of atrazine with BP01 was the control rate reduced relative to the 2 lb/acre treatment with atrazine.

Similarly, the BP01 also improved the control rate of atrazine relative to a mixture of atrazine and crop oil concentrate in all weeds except for Florida Pusley and Primrose. Such an improvement suggests that the bacillus is not acting as a surfactant, but is enhancing effectiveness by either or both of the metabolic activity or translocation characteristics of the co-applied agent.

The preceding are intended solely for purposes of illustrating the invention and are not intended to act as limitations on the scope of the appended claims.

What is claimed is:

1. A method for enhancing the effectiveness of a herbicide by applying to a plant (a) an agriculturally effective active ingredient of a plant growth stunting agent or herbicide; and (b) an enhancer selected from the group consisting of spores, cultures, or suspensions of a suitable Bacillus or soil bacteria.

2. The method of claim 1 wherein siad agriculturally effective active ingredient and said enhancer are applied in a composition.

3. The method according to claim 1 wherein said agriculturally effective active ingredient is a triazine, glyphosate, or sulfosate.

4. The method of claim 1 wherein said enhancer contains a strain of bacteria from the genus Bacillus.

5. The method of claim 1 wherein said enhancer contains a strain of soil bacteria.

6. The method of claim 1 wherein said enhancer contains a *B. cereus.*

7. The method of claim 1 wherein said enhancer contains a *B. cereus* having a characteristic of ATCC 55675.

8. The method of claim 1 wherein said enhancer contains a *B. subtilis.*

9. The method of claim 1 wherein said enhancer contains a *B. subtilis* having a characteristic of ATCC 55675.

10. The method of claim 1 wherein said enhancer contains *B. megaterium.*

11. The method of claim 1 wherein said enhancer contains ATCC 55675.

12. A composition of enhancing the activity of a plant growth regulating agent comprising a suitable Bacillus, spore, culture and suspension thereof and a plant growth stunting agent, wherein the composition does not contain ATCC 55675.

13. The composition of claim 12 wherein said plant growth regulating agent comprises mepiquat chloride.

14. The composition of claim 12 wherein said plant growth regulating agent comprises chlorinequat chloride.

15. The composition of claim 12 wherein the Bacillus is a *Bacillus cereus.*

16. The composition of claim 12 wherein the Bacillus has a characteristic of ATCC 55675.

17. The composition of claim 12 wherein the Bacillus is a *Bacillus subtilis.*

18. A composition for enhancing the activity of an agriculturally effective active ingredient comprising an aqueous mixture comprising: (a) an agriculturally effective active ingredient selected from the group consisting of a plant growth regulating agent, herbicide, systemic fungicide, and a systemic insecticide; and (b) an enhancer selected from the group consisting of spores, cultures, or suspensions of a suitable Bacillus or soil bacteria at a pH sufficiently less than 7 to maintain said enhancer in spore form, provided that the composition does not contain plant growth hormones when said plant growth regulating agent is a plant growth stunting agent.

19. The composition of claim 18 wherein said plant growth regulating agent comprises mepiquat chloride, chlormequat chloride, or ethephon.

20. The composition of claim 18 wherein said agriculturally effective active ingredient comprises a herbicide.

21. The composition of claim 20 wherein the herbicide is a triazine, glyphosate, or sulfosate.

22. The composition of claim 18 wherein said enhancer contains a strain of bacteria from the genus Bacillus.

23. The composition of claim 18 wherein said enhancer contains a strain of soil bacteria.

24. The composition of claim 18 wherein said enhancer contains a *B. cereus.*

25. The composition of claim 18 wherein said enhancer contains a *B. cereus* having a characteristic of ATCC 55675.

26. The composition of claim 18 wherein said enhancer contains a *B. subtilis.*

27. The composition of claim 18 wherein said enhancer contains a *B. subtilis* having a characteristic of ATCC 55675.

28. The composition of claim 18 wherein said enhancer contains *B. megaterium.*

29. The composition of claim 18 wherein said enhancer contains ATCC 55675.

30. A nonliquid composition comprising: a nonliquid mixture of (a) an agriculturally effective active ingredient selected from the group consisting of a plant growth stunting agent, ethephon, a plant growth hormone, naphthalenacetic acid, sodium ortho-nitrophenolate, sodium para-nitrophenolate, sodium 5-nitro-guaicolate, polyhydroxycarboxylic acids of 2, 4, 5, and 6 carbon structures, and a herbicide; and (b) an enhancer containing spores or cultures of a suitable Bacillus or soil bacteria, provided that the composition does not contain plant growth hormones when a plant growth stunting agent is the active ingredient.

31. The composition of claim 30 wherein said active ingredient is mepiquat chloride, chlormequat chloride, or ethephon.

32. The composition of claim 30 wherein said herbicide is glyphosate or sulfosate.

33. A method for increasing the number of fruiting sites on a fruiting plant by a. diluting a composition containing (a) an agriculturally effective active ingredient of a plant growth regulating agent; and (b) an enhancer containing spores of a suitable Bacillus or soil bacteria at a pH of less than 7 and sufficiently low to maintain said Bacillus in spore form, and b. applying the diluted composition to foliage of a plant containing fruiting sites.

34. The method of claim 33 wherein said fruiting plant is cotton.

35. The method of claim 33 wherein said plant growth regulating agent is a plant growth stunting agent or ethephon.

36. The method of claim 33 wherein said enhancer contains a strain of bacteria from the genus Bacillus.

37. The method of claim 33 wherein said enhancer contains a *B. cereus* having a characteristic of ATCC 55675.

38. The method of claim 33 wherein said enhancer contains a *B. subtilis* having a characteristic of ATCC 55675.

39. The method of claim 33 wherein said enhancer contains a *B. megaterium,* a *B. subtilis,* or a *B. cereus.*

40. The method of claim 33 wherein said enhancer contains ATCC 55675.

41. A method for enhancing the effectiveness of an agriculturally effective active ingredient by applying to a plant (a) an agriculturally effective active ingredient of a plant growth stunting agent, ethephon, or a herbicide; and (b) an enhancer selected from the group consisting of spores, cultures, or suspensions of a suitable Bacillus or soil bacteria.

42. The method of claim 41 wherein said agriculturally effective active ingredient is a triazine, glyphosate, or sulfosate.

43. The method of claim 41 wherein said active ingredient is mepiquat chloride or chlormequat chloride.

44. The method of claim 41 wherein said enhancer contains a strain of bacteria from the genus Bacillus.

45. The method of claim 41 wherein said enhancer contains a strain of soil bacteria.

46. The method of claim 41 wherein said enhancer contains a *B. cereus*.

47. The method of claim 41 wherein said enhancer contains a *B. cereus* having a characteristic of ATCC 55675.

48. The method of claim 41 wherein said enhancer contains a *B. subtilis*.

49. The method of claim 41 wherein said enhancer contains a *B. subtilis* having a characteristic of ATCC 55675.

50. The method of claim 41 wherein said enhancer contains *B. megaterium*.

51. The method of claim 41 wherein said enhancer contains ATCC 55675.

* * * * *